(12) United States Patent
Mirizzi

(10) Patent No.: US 6,574,851 B1
(45) Date of Patent: Jun. 10, 2003

(54) STENT MADE BY ROTATIONAL MOLDING OR CENTRIFUGAL CASTING AND METHOD FOR MAKING THE SAME

(75) Inventor: Michael S. Mirizzi, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 64 days.

(21) Appl. No.: 09/629,075

(22) Filed: Jul. 31, 2000

(51) Int. Cl.[7] ................................................ B23F 25/00
(52) U.S. Cl. ...................... 29/527.5; 29/527.1; 264/219
(58) Field of Search ............................. 29/527.1, 527.5; 623/1.11; 264/219; 205/75, 667

(56) References Cited

U.S. PATENT DOCUMENTS 5,569,295 A * 10/1996 Lam .......................... 606/198
5,902,475 A * 5/1999 Trozera et al. .............. 205/655
2002/0050220 A1 * 5/2002 Schueller et al. ........... 101/486

* cited by examiner

*Primary Examiner*—David H. Willse
*Assistant Examiner*—Javier G. Blanco
(74) *Attorney, Agent, or Firm*—Fulwider Patton Lee & Utecht, LLP

(57) ABSTRACT

The invention is directed to an expandable or self-expanding stent for implantation in a body lumen, such as an artery. The stent is made from a centrifugal casting process in which liquid casting material is placed within a female mold which includes an elongated cavity having a angular wall formed of grooves cooperating to form a predetermined stent configuration and rotating the female mold to distribute the casting material throughout the network of grooves. The stent can also be made from a rotational molding process in which dry cold powder resin is placed in a female mold and rotated at low speeds and heated to allow the charge of cold powder material to sinter to form the shape of the stent. The invention is also directed to the method for making such stents made from either centrifugal casting or rotational molding processes.

27 Claims, 8 Drawing Sheets

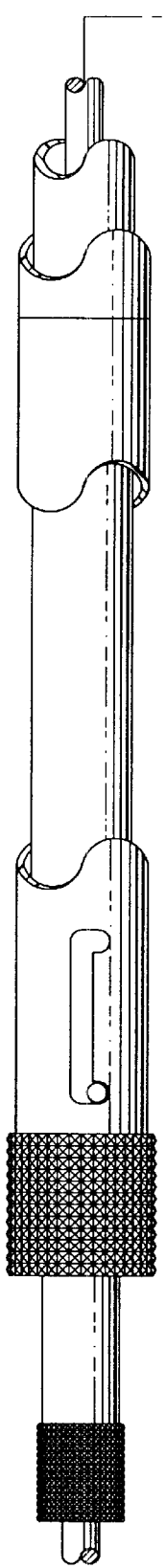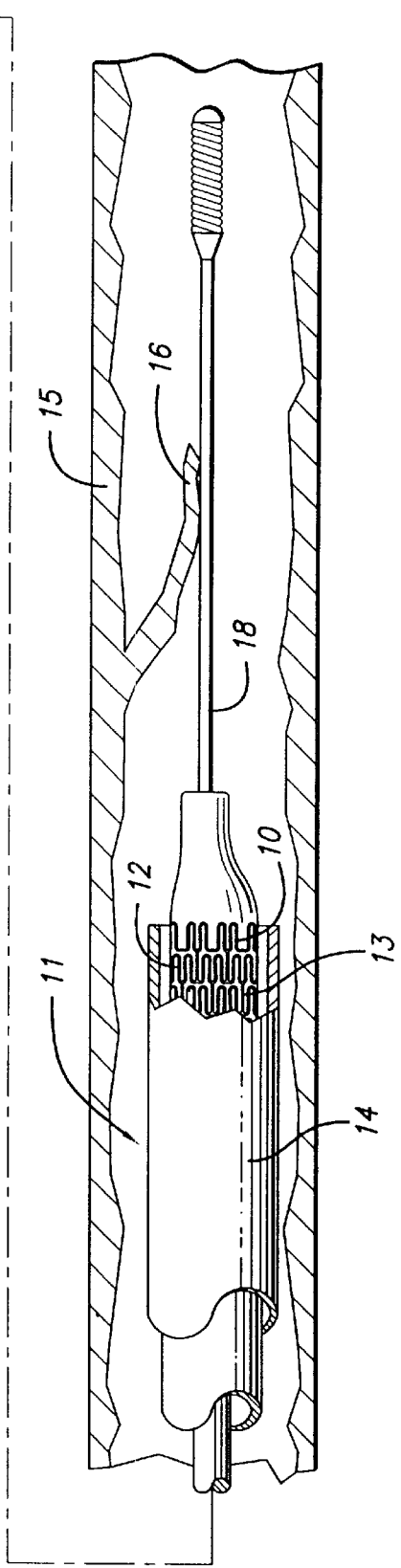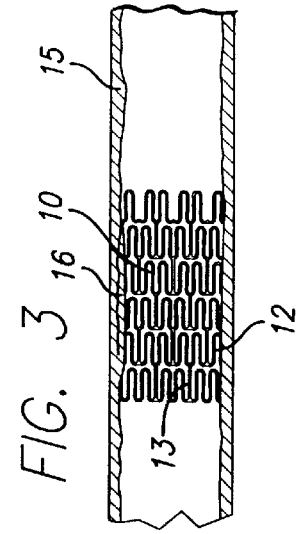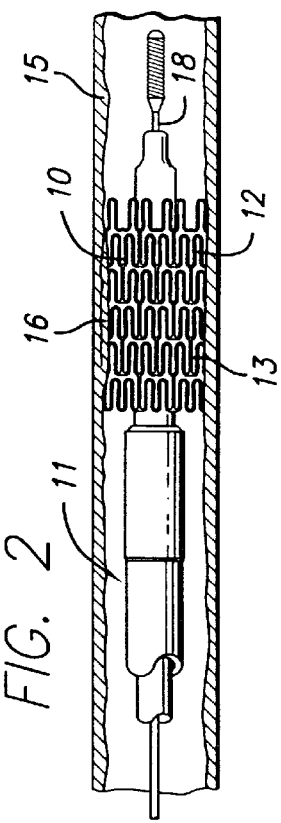

STENT MADE BY ROTATIONAL MOLDING OR CENTRIFUGAL CASTING AND METHOD FOR MAKING THE SAME

BACKGROUND OF THE INVENTION

This invention relates to expandable endoprosthesis devices, generally called stents, which are adapted to be implanted into a patient's body lumen, such as a blood vessel, to maintain the patency thereof. These devices are particularly useful in the treatment and repair of blood vessels after a stenosis has been compressed by percutaneous transluminal coronary angioplasty (PTCA), percutaneous transluminal angioplasty (PTA), or removed by atherectomy, laser angioplasty or other means.

Stents are generally cylindrically shaped devices which function to hold open and sometimes expand a segment of a blood vessel or other anatomical lumen such as a coronary artery. They are particularly suitable for use to support and hold back a dissected arterial lining which can occlude the fluid passageway therethrough.

A variety of devices are known in the art for use as stents and have included coiled wires in a variety of patterns that are expanded after being placed intraluminally on a balloon catheter; helically wound coiled springs manufactured from expandable heat sensitive metals; self expanding stents inserted in a compressed state for deployment in a body lumen, and stents shaped in zig zag patterns. One of the difficulties encountered using prior art stents involve maintaining the radial rigidity needed to hold open a body lumen while at the same time maintaining the longitudinal flexibility of the stent to facilitate its delivery and accommodate the often tortuous path of the patient's vasculature. Generally, the greater the longitudinal flexibility of the stent, the easier and more safely it can be delivered to the implantation site.

Various means have been described to deliver and implant stents. One method frequently described for delivering of a stent to a desired intraluminal location includes mounting the stent on an expandable member, such as a balloon, provided on a distal end of an intravascular catheter, advancing the catheter to the desired location within the patient's body lumen, inflating the balloon on the catheter to expand the stent into a permanent expanded condition, and then deflating the balloon and removing the catheter. Other prior art stent delivery catheters used for implanting self-expanding stents include an inner member upon which the compressed or collapsed stent is mounted and an outer restraining sheath which is placed over the compressed stent to maintain it in its compressed state prior to deployment. When the stent is to be deployed in the body vessel, the outer restraining sheath is retracted in relation to the inner lumen to uncover the compressed stent, allowing the stent to move into its expanded condition.

Stents can be formed from metal alloy tubing, such as stainless steel, along with other biocompatible materials and metal alloys including, but not limited to tantalum and NiTi. Such stents can be made in a number of different ways. One method is to cut a thin wall tubular member to remove portions of the tubing in a desired pattern for the stent, leaving a relatively untouched portions of the metallic tubing which cooperate to form the stent. Machine-controlled lasers are but just one method for cutting the tubing into the desired pattern. Other methods include chemical etchings which remove the portions of the tubing leaving the untouched portions to form the desired pattern for the stent. Still other methods include bending coiled wires in the desired pattern to create the composite stent. Such techniques may include the need to weld and braze coils together to create the composite stent. Such coiled wire stents are often labor-intensive and difficult to achieve a finished product.

The stent structure may be coated with biocompatible coatings to help prevent the body from rejecting the implant. Therapeutic drugs are sometimes coated on the stent surface and are absorbable in the area of treatment over a period of time to help prevent restinosis and to help prevent body rejection of the stent.

It will be apparent from the foregoing that conventional stents are very high precision and, ideally, the most desirable stents usually incorporate a fine precision structure. In this regard, it is important to make precisely dimensioned, smooth, stents in fine geometries without damaging the narrow struts that make up the stent structure. While various cutting processes, including laser cutting and chemical etching have been adequate, improvements have been sought to provide stents of enhanced structural quality at reduced cost.

Accordingly, those concerned with the development, manufacture and use of stents have long recognized the need for improved manufacturing processes for making such stents. The present invention fulfills these and other needs.

SUMMARY OF THE INVENTION

The present invention provides a new and improved method for making a stent. In accordance with the present invention, it is preferred to form the stent using a rotational molding or centrifugal casting process. The present invention also is directed to a vascular stent formed from such a process.

In general, the centrifugal casting process consists of selecting a female rotary mold formed with an elongated cavity having a network of inwardly opening grooves defining a predetermined stent configuration. A charge of casting material, usually in liquid form, is introduced into the cavity and the mold is rotated about a rotational axis to distribute the casting material throughout the mold. The rotational velocity of the mold may be increased to provide greater centrifugal force acting radially outwardly to press the casting material into grooves which define the structure of the stent. The casting material is then allowed to solidify forming a cast stent having a predetermined configuration.

The interior surface of the female mold is formed with a plurality of circumferential grooves and interconnecting channels. For example, each circumferential groove can have a continuous undulating pattern formed from a plurality of U-shaped pathways linked together in a consecutive alternating inverted relationship to provide a generally serpentine configuration. Interconnecting channels extend longitudinally between adjacent circumferential grooves connecting them together. Thus, the grooves and channels cooperate, when substantially filled with casting material, to provide a casting which provides a predetermined stent structure.

A charge of casting material preferably is introduced into the mold cavity at a predetermined rate to spread the material over the entire mold length in one continuous flow. It should be appreciated that the casting material may be introduced into the mold cavity while the mold is stationary or when it is rotating.

When the charge of casting material is introduced into the mold cavity and the mold is rotated, frictional forces develop between the casting material and the surface of the mold.

Thus, the casting material is rotationally accelerated as it fills the grooves and channels provided in the mold surface. As the casting material fills the mold, centrifugal force from the rotating mold provides a pressure gradient acting radially across the thickness of the casting.

During the centrifugal casting process, the female mold is rotated at a sufficient tangential velocity to impart some centrifugal acceleration to the casting material. The centrifugal acceleration prevents slippage between newly introduced casting material and either the rotating mold surface or a previously deposited layer of material. In addition, centrifugal force helps prevent the casting material from falling out of the mold as it passes over the top arcuate section of the mold cavity.

After the charge of casting material has substantially filled the mold, the rotational speed of the mold may be increased while the casting material is allowed to solidify. By increasing the rotational speed of the mold during solidification, greater centrifugal force is applied to the casting material, making it possible to produce dense castings of high quality. It will be appreciated that the favorable thermal gradient and the radially outward acting centrifugal force produced by the rotating mold influence the solidification of the casting. As a result, porosity in the material sometimes occurs during the solidification of a casting material can be eliminated. However, if desired, a stent made in accordance with the present invention could be made porous to allow a therapeutic drug to be added to the surface or into the casting itself to produce a suitable drug delivery stent.

Rotational molding is another method for producing a stress-free stent having intricate strut patterns. Some of the steps for manufacturing a rotationally molded stent are very similar to the centrifugal casting process. The rotational molding process includes selecting a female rotary mold formed with an elongated cavity having a network of inwardly open grooves defining a predetermined stent configuration. However, the rotational molding process utilizes lower speeds than the centrifugal casting process. Normally, in rotational molding, the speed is in a range of about 5 to 20 rpms. The casting material for the rotational molding process is usually a dry powder, as opposed to a liquid, which is usually used in the centrifugal casting process. Therefore, as opposed to the centrifugal casting process, the casting material remains at the bottom of the rotating cavity of the mold, due to the force of gravity. As a result, in a rotational molding, the casting material stays in loose powder form until the surface of the mold reaches a temperature level that is high enough for the particles of the casting material to begin to adhere or sinter to the mold or each other at the layer nearest to the heated surface of the mold. Additionally, the female rotary mold is pre-charged cold with cold powder resin acting as the casting material. As the mold cavity is rotated, it is also heated to reach the temperature necessary to begin the sintering process. The heat source is eventually removed after a predetermined length of time and the mold is allowed to cool to solidify the casting material. As the material solidifies, a uniform melt structure is achieved.

A stent made in conjunction with the rotational molding process results in a stress-free structure which, as with the centrifugal casting process, can be formed in various complicated strut patterns. The precision of the stent will be determined by the precision in which the female rotary mold is formed. Stents made in conjunction with the present invention can be made from polymeric materials, including thermal plastic and thermal set polymers, and other biocompatible materials such as metal alloys including, but not limited to, tantalum, NiTi, as well as stainless steel 316L. The present process can be used to create stents of virtually any design.

The above and other objects and advantages of this invention will be apparent from the following more detailed description when taken in conjunction with the accompanying drawings of exemplary embodiments.

BRIEF DESCRIPTION OF THE DRAWINGS

FIG. 1 is a side view, partially in section, of a stent embodying features of the present invention mounted on a delivery catheter and disposed within a damaged artery.

FIG. 2 is a side view, in reduced scale, similar to FIG. 1 wherein the stent is expanded within a damaged artery, pressing the damaged lining against the arterial wall.

FIG. 3 is a side view, partially in section showing the stent of FIG. 2 expanded against the wall of the artery after withdrawal of the delivery catheter.

DETAILED DESCRIPTION OF THE PREFERRED EMBODIMENTS

Figure 4:
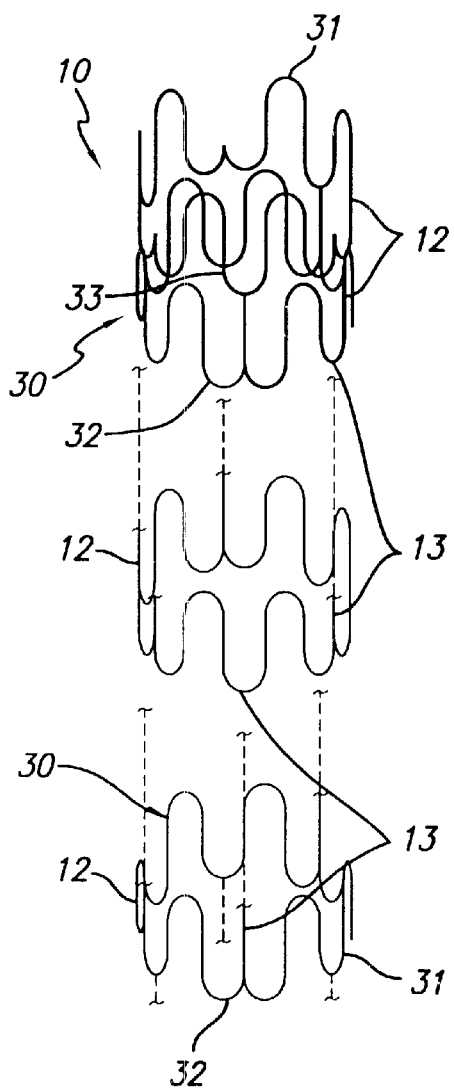
FIG. 4 is an exploded perspective view, in enlarged scale, of the stent shown in FIG. 1 but in its unexpanded state.

Referring now to the drawings, in which reference numerals represent like or corresponding elements across the drawings, and particularly FIGS. 1–3 thereof, there is generally shown a stent 10 made in accordance with the present invention which is mounted onto a delivery catheter 11. The stent 10 is a high precision patterned tubular device, which in the embodiment shown in FIG. 1 is a self-expanding stent which helps to hold and maintain open a portion of an artery and prevent restenosis from occurring in the area of treatment. The stent 10 typically comprises a plurality of radially expanded cylindrical elements 12 disposed generally coaxially and interconnected by elements 13 disposed therebetween adjacent cylindrical elements 12. The delivery catheter 11 includes a restraining sheath 14 which extends over the contracted stent 10 until the stent 10 is ready for deployment within an artery 15, or other blood vessel or body vessel of a patient. The artery 15, as shown in FIGS. 1–3, has a dissected lining 16 which has occluded a portion of the arterial passageway.

Each radially expandable cylindrical element 12 of the stent 10 may be independently expanded. Therefore, the shape of the stent can be other than cylindrical, e.g. tapered, to facilitate implantation of the stent 10 in a variety of body lumen shapes.

The delivery of the stent 10 is accomplished in the following manner. The stent 10 is first mounted onto an inner tubular member on the distal extremity of the delivery catheter 11 with the restraining sheath 14 placed over the contracted stent 10. The catheter-stent assembly is introduced within the patient's vasculature in a conventional Seldinger technique through a guiding catheter (not shown). A guide wire 18 is disposed across the damaged arterial section with the detached or dissected lining 16 and then the catheter-stent assembly is advanced over a guide wire 18 within the artery until the stent is directly under the detached lining 16. The restraining sheath 14 is then retracted, allowing the stent to expand to a larger diameter to press up against the artery, which is illustrated in FIG. 2. While not shown in the drawing, the artery is preferably expanded slightly by the expansion of the stent to seat or otherwise fix the stent to prevent movement. In some circumstances during the treatment of stenotic portions of an artery, the artery may have to be expanded considerably in order to facilitate passage of blood or other fluid therethrough.

The stent 10 shown in FIGS. 1–5 is directed to a self-expanding stent which can be made from a polymeric material, NiTi, or similar material. However, a stent made in accordance with the present invention could be either self-expanding or balloon expandable, depending upon the type of material utilized to manufacture the stent. It should also be appreciated that although the stent 10 is shown being using holding up a detached lining in an artery of a patient, the stent could also be utilized to treat an area in which atherosclerotic plaque has built up against the wall of the artery. Moreover, a stent made in accordance with the present invention could be utilized in any one of a number of different body vessels, including but not limited to carotid arteries, coronary arteries and renal arteries. The stent could be used for primary stenting purposes, i.e., to directly enlarge the opening in the artery or it could be utilized in conjunction with predilitation in which plaque is initially expanded in the area of treatment by a balloon dilitation catheter. Thereafter, the stent could be placed in the predilitated area of treatment.

FIG. 4 is an enlarged perspective view of the stent 10 shown in FIG. 1 with one end of the stent shown in a exploded view to illustrate in greater detail to show just one example of a stent structure which can be made in accordance with the present invention. Each pair of the interconnecting elements 13 on one side of a cylindrical element 12 is preferably placed to achieve maximum flexibility for a stent. In the embodiment shown in FIG. 4, the stent has three interconnecting elements 13 between adjacent radially expandable cylindrical elements 12 which are 120 degrees apart. Each pair of interconnecting elements 13 on one side of a cylindrical element 12 are offset radially 60 degrees from the pair on the other side of the cylindrical element. The alternation of the interconnecting elements results in a stent which is longitudinally flexible in essentially all directions. Various configurations for the placement of interconnecting elements are possible. All of the interconnecting elements of an individual stent could be secured to either the peaks or valleys of the undulating structural elements in order to prevent shortening of the stent during expansion thereof.

Figure 5:
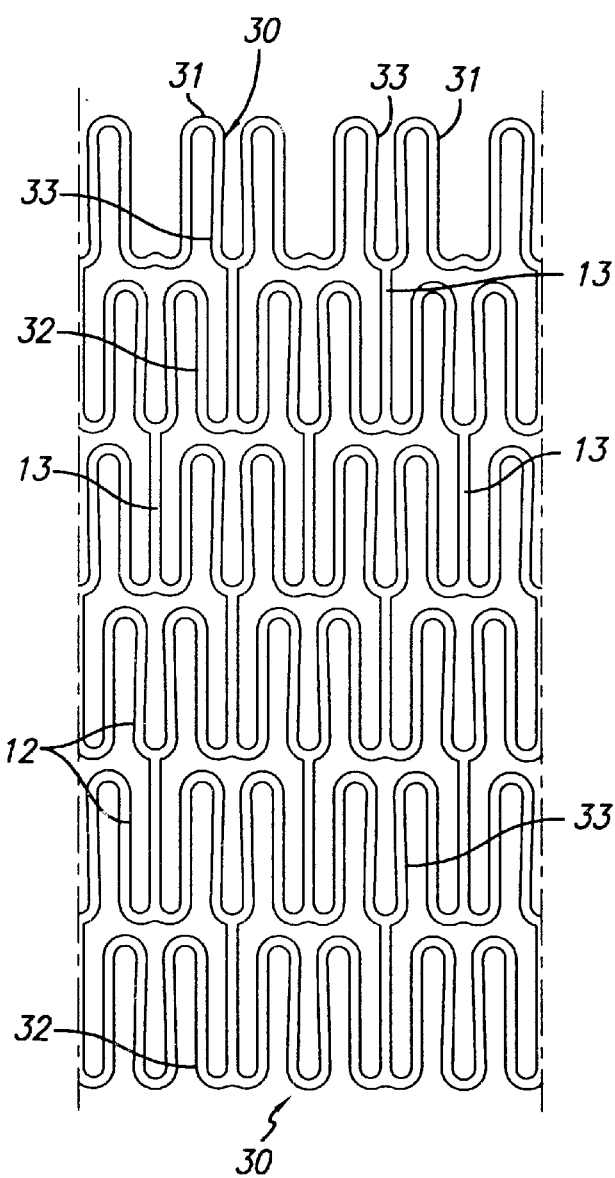
FIG. 5 is a plan view, in enlarged scale, of a flattened section of a stent shown in FIG. 4.

The number of undulations may also be varied to accommodate placement of interconnecting elements 13, e.g. at the peaks of the undulations or along the sides of the undulations as shown in FIG. 5.

As best observed in FIGS. 4 and 5, cylindrical elements 12 are in the form of a serpentine pattern 30. As previously mentioned, each cylindrical element 12 is connected by interconnecting elements 13. Serpentine pattern 30 is made up of a plurality of U-shaped members 31, W-shaped members 32, and Y-shaped members 33, each having a different radius so that expansion forces are more evenly distributed over the various members.

It should be appreciated that the present invention can be used to make stents which do not incorporate cylindrical rings as described herein, but rather, other structural elements, such as zig zag patterns, coil patterns, and the like to create a composite stenting device.

The stent 10 illustratively described above, and similar stent structures, can be made in many ways. However, a preferred method of making the stent is to mold or cast the desired cylindrical body having a predetermined reticulated structure. In accordance with the present invention, it is preferred to form the stent using a rotational molding or centrifugal casting process.

In general, the centrifugal casting process and rotational molding process begins by selecting a female rotational mold formed with an elongated cavity having a predetermined stent configuration. The interior surface of the female mold can be formed with a serpentine pattern of circumferential grooves and interconnecting channels. For example, each circumferential groove may have a continuous undulating pattern formed from a plurality of U-shaped pathways linked together in a consecutive alternating inverted relationship to provide a generally serpentine configuration. Interconnecting channels extend longitudinally between adjacent circumferential grooves connecting them together. Thus, the grooves and channels cooperate to, when substantially filled with casting material, provide a casting which provides a predetermined stent structure.

A measured charge of casting material is added to the female mold wherein the mold is rotated about a horizontal axis. As the female mold rotates, the casting material travels about the mold to substantially fill the cylindrical grooves and associated interconnecting channels. In the centrifugal casting process, the rotational speed of the female mold provides a sufficient tangential velocity such that centrifugal acceleration presses the casting material radially outwardly within the grooves and channels. While the casting material is retained within the grooves and channels, the material is allowed to solidify, thereby forming the desired stent structure. In the rotational molding process, the casting material, usually a dry or cold plastic powder or resin mixture, is placed in the female mold. The female mold cavity is heated as it is being rotated, at a slower speed than the centrifugal casting process. The cold plastic powder eventually liquifies to some extent as the powder sinters to create a uniform structure which takes the shape of the mold, i.e., a stent having a predetermined strut pattern.

Figure 6:
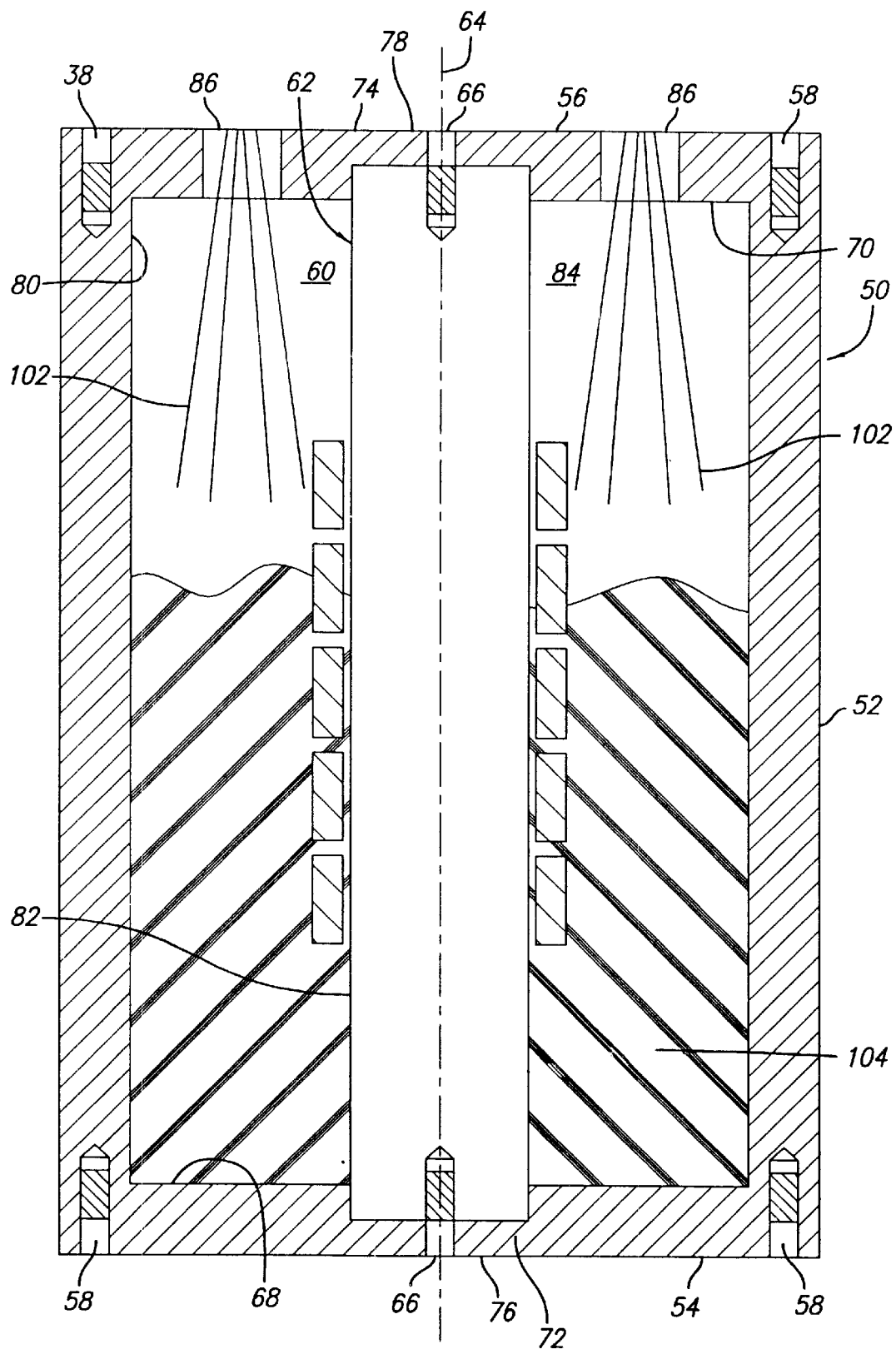
FIG. 6 is a diagrammatic cross-sectional view of a casting flask containing a male tooling die which may be filled with a selected material to form a female mold having a network of grooves providing the undulating pattern of the stent of FIG. 4.

Referring now to FIG. 6, the female mold is formed in an elongated casting flask, generally designated 50. The casting flask 50 consists of a hollow elongated flask body 52 having a generally circular, square, or hexagonal transverse cross-section. A base plate 54 closes at one end of the flask body and a cover plate 56 closes the other end. The base plate 54 and cover plate 56 are shaped to fit over the ends of the flask body and are mechanically fastened thereto with bolts or screws 58 as shown in FIG. 6.

The base plate 54, cover plate 56 and flask body 52 cooperate to define a cylindrical chamber 60 disposed therebetween. A cylindrical male tooling die 62 is mounted axially in the center of the chamber 60 and aligned with the longitudinal axis 64 of the flask 50. The tooling die 62 extends the length of the flask body 52 and is mechanically fastened to the base plate 54 and the cover plate 56 with bolts or screws 66. As shown in FIG. 6 the inner surface 68 of the base plate 54 and the inner surface 70 of the cover plate 56 are formed with respective cylindrical recesses 72, 74 which are sized to slidably receive the respective first and second ends 76, 78 of such male tooling die.

The inner wall 80 of the chamber 60 and the exterior surface 82 of the male tooling die 62 cooperate to define an annular female mold chamber 84. The cover plate 56 is formed with inlet orifices 86 which provide fluid passageways wherein mold material may be introduced from outside the casting flask 50 to fill the portion of the chamber 60 defining the female mold area 84.

Figure 7:
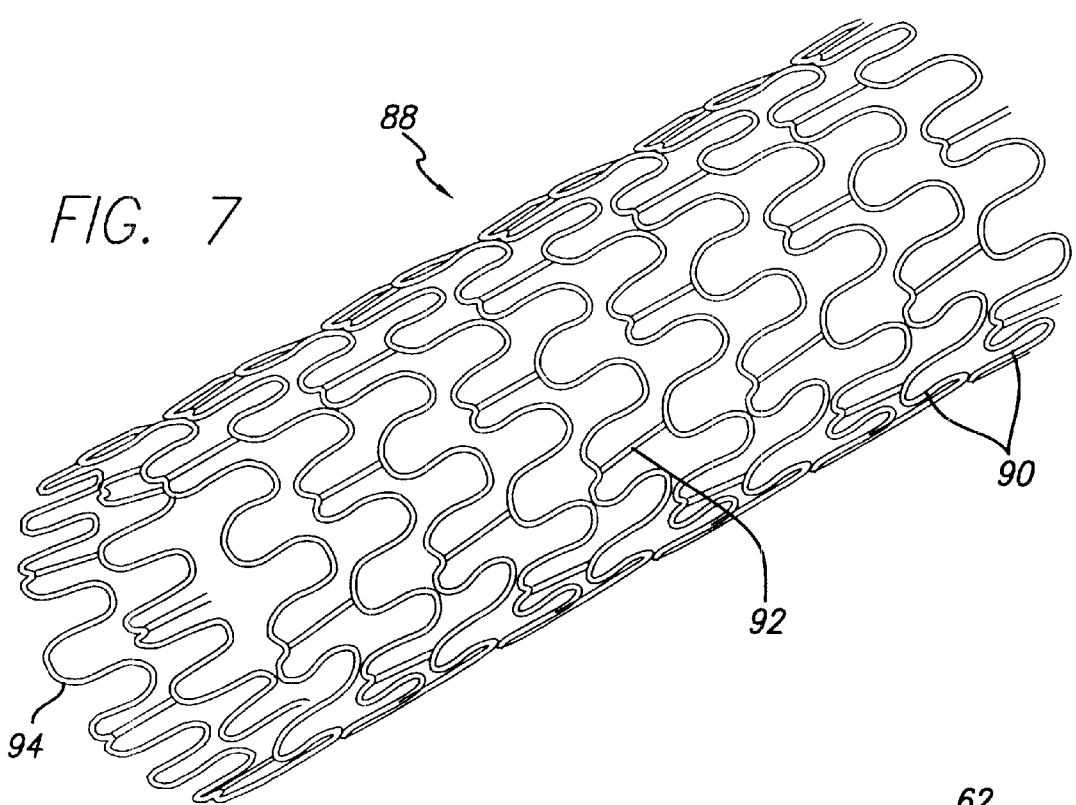
FIG. 7 is a perspective view, reduced in scale, of a stent pattern which may be incorporated in the male tooling die of FIG. 6.
Figure 8:
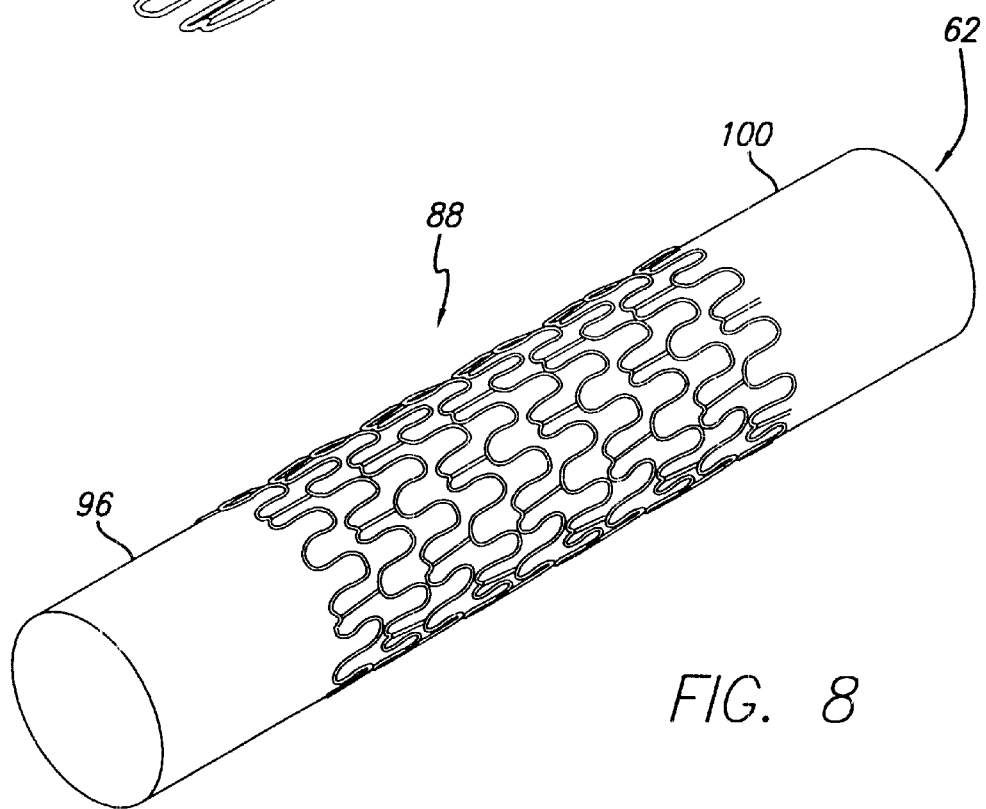
FIG. 8 is a perspective view, reduced in scale, of the male tooling die of FIG. 6.

Referring now to FIGS. 7 and 8, mounted on the external surface 96 of the male tooling die 62 is a male mold model/pattern 88 configured with a plurality of undulating cylindrical rings 90 generally spaced longitudinally apart about an axis and interconnected by one or more axial interconnecting members 92, all cooperating together to mimic a shape comparable to the stent 10 shown in FIGS. 1–4. The individual rings 90 consist of a plurality of U-shaped structures 94 linked together to provide a continuous undulating pattern.

It is envisioned that the male mold model/pattern 88 is formed by using existing stent cutting technology such as that described in U.S. Pat. No. 5,759,192 to Saunders wherein the stent pattern is produced by direct laser cutting the desired stent structure from a single metal tube.

Typically, the stent pattern is laser cut to provide the structural male mold of a stent in the unexpanded condition. However, the stent pattern may also be laser cut to provide the structural pattern of a male mold model in the expanded condition. It is also contemplated that an unexpanded stent pattern may be radially expanded to an enlarged second diameter by a balloon catheter or similar device. By radially expanding a stent pattern from an unexpanded condition to an enlarged second diameter, molds possessing various stent patterns having a variety of inner diameters may be produced for production purposes.

Whether the stent pattern is utilized in the unexpanded or expanded condition depends upon how the casted stent will be deployed during implantation in the body lumen. For example, many stents manufactured from metal alloys are deployed by mounting the unexpanded stent onto an expandable balloon catheter. At the desired location within the body lumen, the balloon catheter is inflated to expand the stent radially. During balloon inflation, the cylindrical elements of the stent are plastically deformed when expanded so that the stent will remain in the expanded condition and therefore will be sufficiently rigid to prevent the collapse thereof in use. For this type of deployment, such a stent made in accordance with the present invention is centrifugally cast or rotationally molded in the unexpanded condition. Therefore, an unexpanded male mold model is required to form a suitable female mold.

Stents made in accordance with the present invention from shaped-memory alloys, such as NiTi, or polymeric based resin materials are deployed differently. For example, a stent made from NiTi or polymeric-based resin materials is self-expanding. This is because plastic deformation is not practical in shaped-memory alloys and polymeric materials. Thus, the stent is centrifugally cast or rotationally molded in the expanded condition. In order to facilitate deployment within the body lumen, the stent is compressed from its expanded condition to a low profile to be disposed within the delivery catheter. As explained above, a retractable protective delivery sheath is mounted about the exterior of the stent. The delivery sheath captures the stent and secures it against the inner member of the delivery catheter until the stent is ready for deployment. The delivery sheath is retracted at the desired location within the body lumen, and the stent is allowed to self-expand, returning to its original expanded condition. Therefore, an expanded stent pattern is required to form a suitable female mold.

As shown in FIG. 8, the male mold model/pattern 88 is slidably mounted about the circumference of a cylindrical core pin 96. The inside diameter of the male mold model/pattern 88 and the outer surface 100 of the core pin 96 are closely toleranced so that a slight interference fit exists as the stent pattern is mounted about the core pin. As a result, the mold model/pattern 88 and underlying core pin 96 cooperate to form the male tooling die 62 (FIG. 6).

Such die is mounted in the flask 50, as shown in FIG. 6. Liquid or molten mold material 102 is then poured into the chamber 60 through orifices 86. The mold material 102 flows about the portion of the chamber defining the female mold area 84 thereby filling the annular space between the outer surface 82 of the male tooling die 62 and the inner wall 80 of the chamber 60. The mold material 102 is allowed to solidify to form the female mold 104.

Figure 9:
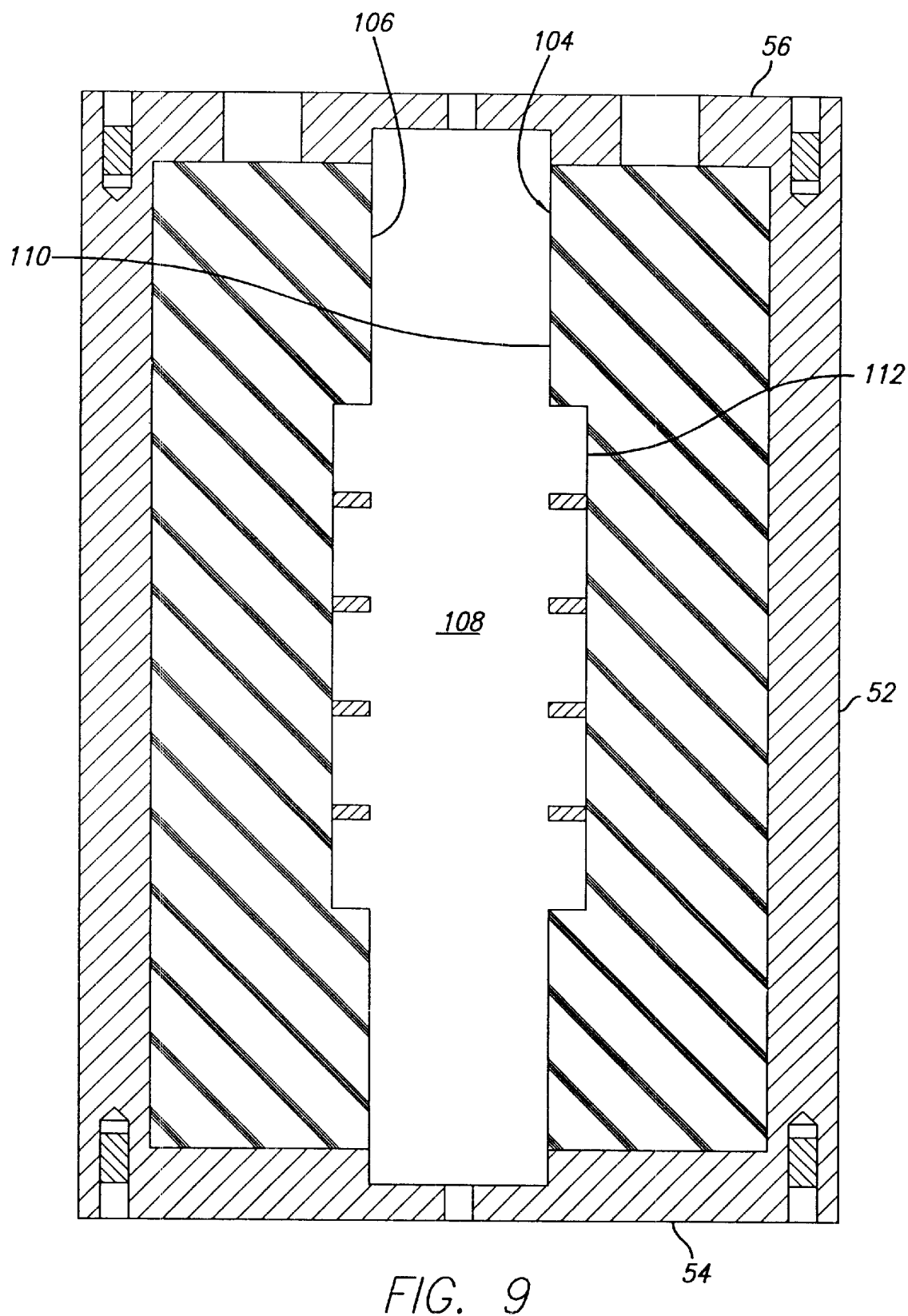
FIG. 9 is a cross-sectional view, in reduced scale, of the casting flask containing a female mold as formed in FIG. 6.

Referring now to FIG. 9, when the male tooling die is removed, the resulting female mold 104 consists of an interior cylindrical mold wall 106 defining a cylindrical cavity 108. The interior surface 110 of the female mold 104 is formed with a plurality of circumferential grooves 112 having a continuous undulating pattern corresponding with the male model/pattern 88 shown in FIGS. 7 and 8. The circumferential grooves 112 are formed with a plurality of U-shaped pathways linked together in a consecutive alternating inverted relationship. In addition, interconnecting channels extend longitudinally between adjacent circumferential grooves connecting them together.

It is envisioned that the female mold 104 may be made of metal, graphite, ceramic, silicone, plastic or other similar materials. However, molds which are capable of being used repeatedly for the production of many castings are generally preferred. Therefore, functional requirements of the mold and thermal conditions to which the mold will be exposed often dictate the material selection. For example, when casting a stent with molten metal, the female mold 104 must be formed with a material which is suitable for withstanding elevated temperatures. Similarly, stents casted with a powdered polymeric casting material which is introduced into the mold cavity and then sintered in the mold will also require a heat resistant molding material. In contrast, when casting a stent with a liquid thermoset polymer, the ability to withstand elevated temperatures may not be a critical consideration for the associated mold design.

Those skilled in the art will appreciate that when the female mold 104 is heated it expands and when the mold is cooled it contracts. Therefore the mold will typically fail by the formation of thermal fatigue cracks which result from internal stress which are produced as a result of thermal gradients extending through the cross section. To avoid thermal fatigue failures, a thin mold wall 106 is desired because stresses resulting from thermal gradients within the mold cross section are minimized. However, a mold wall 106 that is too thin in comparison to the casted body may result in making it virtually impossible to remove the final product. This may occur since the thin wall of the mold will cool more rapidly than the casting contained therein, causing the mold to shrink around the hot casting.

In addition, if the mold wall 106 is too thin, the mold may be subject to warpage. As a result, after only a very few castings, the mold may warp making it impossible to remove the casting. Thus, it is necessary that the mold be thick enough and heavy enough to ensure dimension stability. Naturally, short molds will warp less then longer molds. Accordingly, longer molds will require heavier mold wall cross sections.

It is also necessary that the female mold 104 be heavy enough to absorb the amount of heat that is given off during the solidification process in making the casting. The mold 104 must be able to absorb the latent heat of fusion of the metal or polymer being cast, the superheat of the metal above the solidification temperature, plus some of the heat given off by the casting as it cools to the temperature at which it is extracted from the mold. Therefore, if the mold wall 106 is too thin, with respect to the casting being produce, the mold 104 will attain excessive temperatures. Thus, the mass of the mold itself must be adequate to absorb a sudden impact of heat from the molten casting material.

Figure 10:
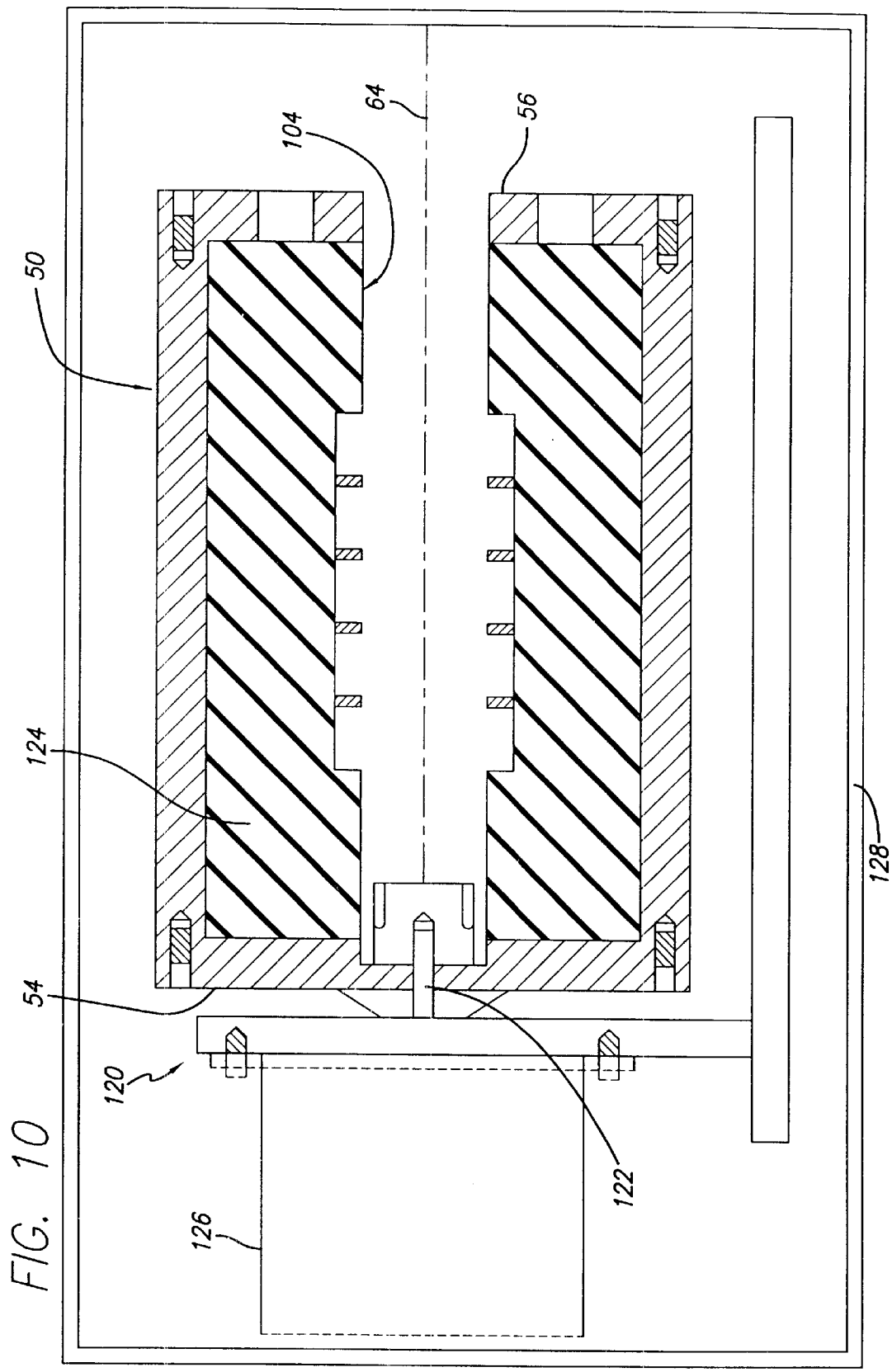
FIG. 10 is a cross-sectional view, in reduced scale, of the casting flask containing the female mold, as shown in FIG. 6, attached to a horizontal-axis centrifugal casting/rotational molding machine.

The female mold 104 may be mounted in the casting flask 50 to be attached to a centrifugal casting machine 120 (FIG. 10). While the use of a horizontal-axis centrifugal casting machine will be discussed in greater detail below, vertical or inclined casting machines may also be used.

As illustrated in FIG. 10 the casting flask 50 is attached to the spindle 122 of a casting machine 120. The spindle 122 extends through the base plate 54 of the flask 50 where it is retained by a locking collar 124. A motor 126 drives the spindle 122 to rotate the casting flask 50 about the longitudinal axis 64 at a desired rotational velocity.

For stents casted with metal alloy, the mold 104 should be heated prior to casting. One method for heating the mold 104 is to place the entire casting flask 50 containing the mold in an oven external to the casting machine 120. The entire flask 50 is then heated by conduction, induction, or irradiation until the desired mold temperature is achieved. The flask is then removed from the oven and placed in the casting machine 120 at the proper time for production.

It is also envisioned that the mold may be heated by attaching the casting flask to the casting machine and placing the entire assembly in an oven 128 (FIG. 10). In addition, the mold 104 may be heated externally by gas burners or it can be heated internally by hot air provided by gas heaters. When the female mold 104 is heated in the casting machine 120 during the rotational molding process, the mold should be rotated slowly to distribute the heat evenly throughout the mold.

Figure 11:
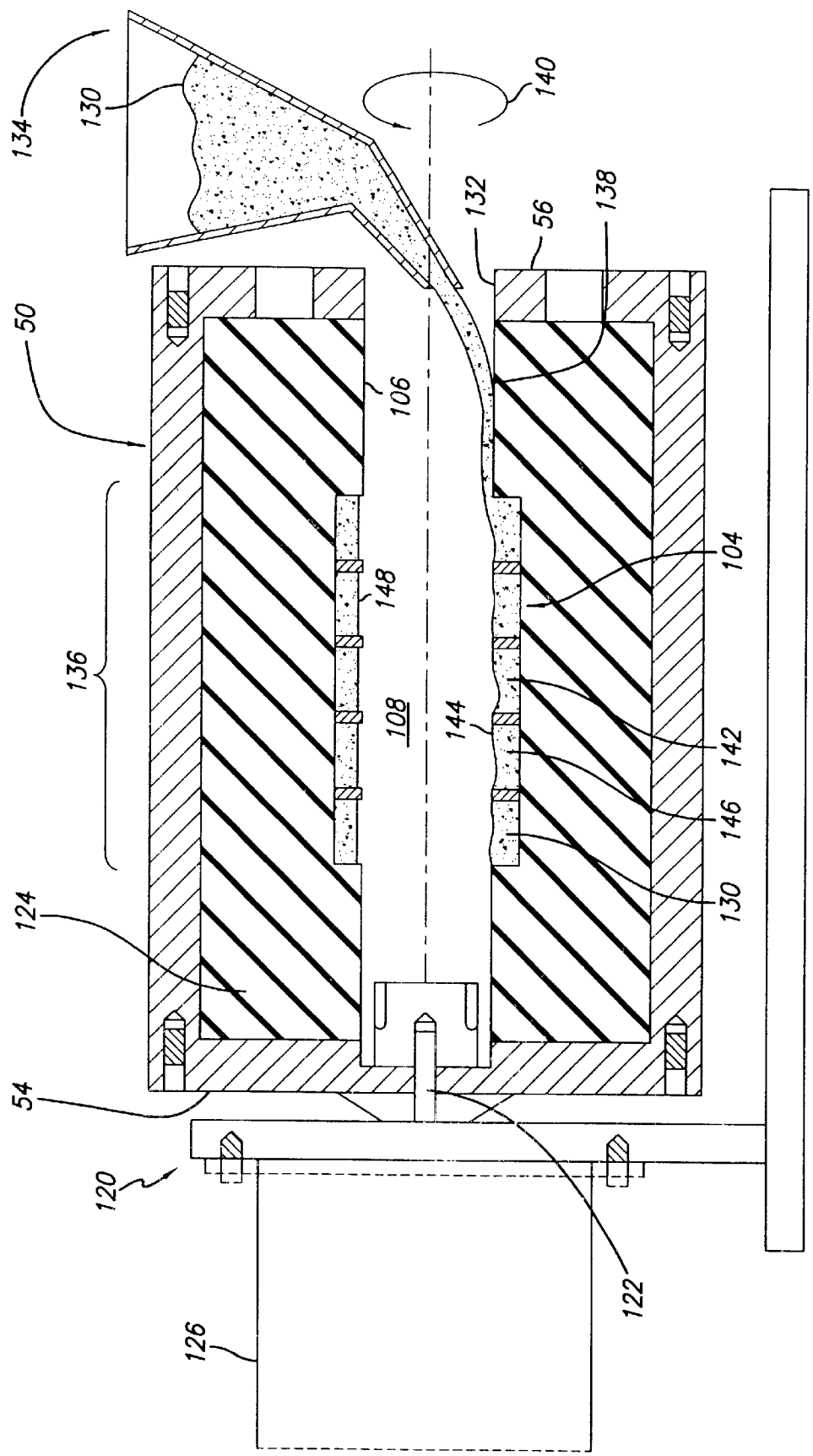
FIG. 11 is a cross-sectional view of the casting flask and horizontal-axis centrifugal casting/rotational molding machine shown in FIG. 10 showing the casting material being introduced into the female mold.

Referring now to FIG. 11, a charge of casting material 130 may be introduced into the rotating mold cavity 108 through a hole 132 formed in the cover plate 56. The charge of casting material 130 is poured from a spout, generally designated 134 at a predetermined rate to spread over the entire mold length 136 preferably in one continuous flow. In practice a predetermined amount of casting material 130 is introduced into the cavity 108 to substantially fill the female mold 104. It is envisioned that the casting material may be introduced into the mold cavity while the mold is stationary or when it is rotating.

During the centrifugal casting process, when the charge casting material 130 is introduced onto the inner surface 138 of a rotating mold 104, all of it will not be accelerated immediately. Instead, rotational velocity, generally designated 140, is imparted to the casting material by virtue of frictional forces developed between the casting material 130 and the surface of the mold 138. After the inner mold surface is covered with a layer of casting material, additional casting material is accelerated by internal friction between the rotating casting material and the material to be accelerated.

When the mold 104 is rotating at the optimum speed, newly introduced casting material will be accelerated rapidly and held firmly to the inner surface of the mold 138. As the casting material fills the mold 104, centrifugal force from the rotating mold provides a pressure gradient acting radially across the thickness of the casting 142. The pressure is lowest at the inner surface 144 of the casting, increasing to a maximum at the outer surface 146 of the casting.

During the centrifugal casting process, the female mold 104 can be rotated at a sufficient tangential velocity to impart a centrifugal acceleration. In some cases, a centrifugal acceleration of greater than 1G (the force of gravity) may be applied to the casting material. Centrifugal acceleration prevents slippage between newly introduced casting material 130 and either the rotating mold surface 138 or the previously deposited layer of material. At the moment when newly introduced casting material passes over the top arcuate section 148 of the center of the cavity 108 for the first time, it is moving at only a fraction of the full rotational speed. It is not until later that inertia is overcome and the casting material is accelerated to the mold rotational speed.

Based upon the diameter of the cylindrical cavity 108 formed by the female mold 104, there is a tangential velocity below which centrifugal force cannot prevent the casting material 130 from falling out of the mold as it passes over the top arcuate section 148 of the center of the cavity 108. This tangential velocity establishes a minimum rotational speed to which the casting material filling the female mold must be accelerated. At higher rotational speeds, the casting material will be held in place with increasing force.

It will be appreciated that several conditions play a major role in determining the optimum rotational speed for the mold when the casting material 130 is being introduced. First, in order to oppose gravity, thereby holding the casting material 130 in the female mold 104, the casting material must be centrifugally accelerated above 1G. Alternatively, because friction plays an important part in accelerating the casting material, the tangential velocity at the mold surface is also an important consideration. Finally, the degree to which the casting material can be accelerated is a function of friction. Frictional forces increase with surface roughness, casting material viscosity, and the speed of the solidification. In light of these variables, is not possible to calculate an optimum mold rotation speed for pouring the casting material. Therefore, in most cases, casting rotational speeds are determined by trial and error.

After the charge of casting material 130 has substantially filled the grooves in the female mold 104, the rotational speed of the mold may be increased and the casting material is allowed to solidify. By increasing the rotational speed of the mold during solidification, greater centrifugal force is applied to the casting material, making it possible to produce dense castings of high quality.

During solidification, essentially all of the heat associated with a molten casting material is extracted through the mold wall 106. Therefore, molten casting material will solidify from the outer surface of the casting 146 to the inner surface of the casting 144. It will be appreciated that the favorable thermal gradient and the radially outward acting centrifugal force produced by the rotating mold influence the solidification of a molten casting. As a result of this interaction, each successive increment of casting material to solidify is fed by the residual casting material in contact with it until solidification is complete. Thus, the possibility of eliminating porosity which often occurs during the solidification of a molten material can be accomplished.

Figure 12:
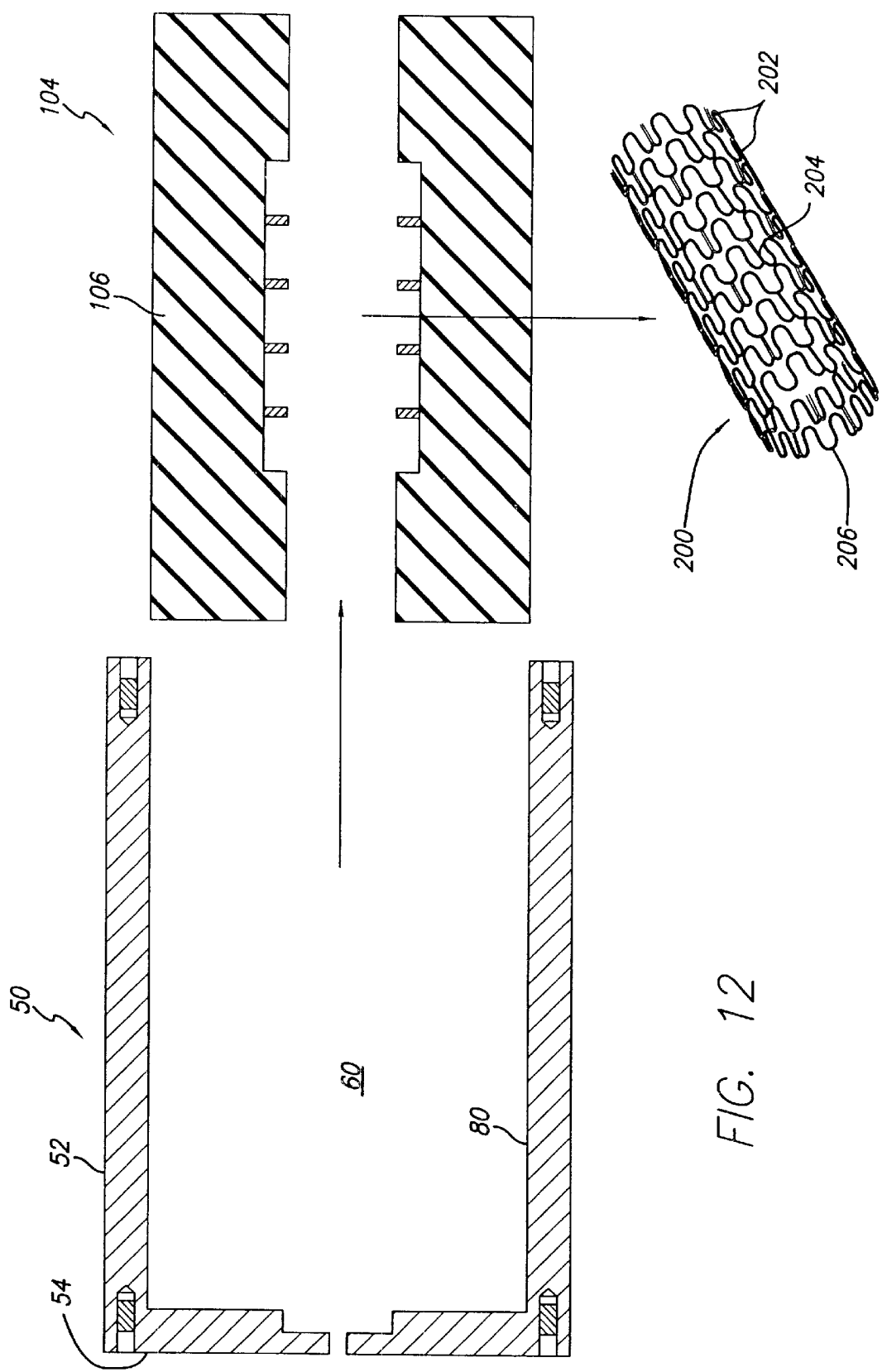
FIG. 12 is an exploded cross-sectional view of the female mold removed from the casting flask shown in FIG. 6 and the centrifugally cast/rotationally molded stent as it is removed from the female mold.

Referring now to FIGS. 11 and 12, once the casting 142 has solidified, the casting flask 50 may be removed from the casting machine 120. The cover plate 56 may be removed from the casting flask 50 and the female mold 104 containing the casting 142 is slidably extracted from the chamber 60. Thereinafter, casted stent 200 may be removed from the female mold 104.

It will be appreciated that the casted stent 200 is configured with a plurality undulating cylindrical rings 202 generally spaced longitudinally apart on about an axis and interconnected by one or more longitudinal interconnecting struts 204. The individual cylindrical rings 202 consist of a plurality of U-shaped structures 206 linked together to provide a continuous undulating pattern. However, the present process can be used to create stents of virtually any design.

It is envisioned that the stent 200 may be casted from a stainless steel of the type 316L, or from other biocompatible materials and metal alloys including, but not limited to tantalum, NiTi, as well as thermoplastic and thermoset polymers.

In addition, it is also envisioned that powdered casting materials such as polymeric based resins can be used in the present invention to produce non-metallic stents of superior quality. Those skilled in the art will realize that when powdered casting materials are used, the powdered form of the material will be introduced into the mold cavity and then heated to allow the dry powder to melt somewhat and sinter together to form a uniform plastic structure. Thereinafter, the mold is rotated as discussed above, to help mix the dry powder casting material and to help maintain the casting material within the mold. After the polymer has substantially filled the mold, the mold is pulled out of the oven and the rotational speed of the mold is maintained while casting material is allowed to solidify. Finally, the mold is opened and the formed stent is removed.

Casting materials may also be combined with suitable drug agents to produce a casted stent which is capable reducing the incidence of restenosis. As such, it is envisioned that antiplatelet agents, anticoagulant agents, antimicrobial agents, anti-inflammatory agents, antimetabolic agents and the like may be supplied to the localized area of treatment by the stent structure.

It should be appreciated that although the centrifugal casting/rotational molding process is shown with the female mold being rotated in a horizontal axis, it is also possible to rotate the mold in a vertical axis as well. Additionally, the female mold could also be bi-axially rotated about a horizontal and vertical axis, if desired.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed:

1. A method of making a stent of a predetermined configuration including:

selecting a female mold formed with an elongated cavity having an annular wall formed with a network of grooves cooperating to form a predetermined stent configuration;

introducing a charge of casting material into the cavity;

rotating the female mold about a rotational axis to distribute the casting material throughout the network of grooves to form the predetermined stent configuration; and solidifying the casting material to form the stent.

2. The method of claim 1, wherein:

selecting the female mold formed with an elongated cavity includes:
creating a model/pattern of a stent;
placing the model/pattern of the stent on a tooling die; and
pouring mold material over the tooling die to form the female mold.

3. The method of claim 1, further including:

heating the female mold while the female mold is being rotated.

4. The method of claim 3, further including:

cooling the female mold after the female mold has been heated for a predetermined time.

5. The method of claim 4, wherein:

the female mold is still being rotated as the female mold is being cooled.

6. The method of claim 1, wherein:

the casting material is a cold powder resin.

7. The method of claim 1, wherein:

the casting material is a liquid-pourable casting material.

8. The method of claim 1, wherein:

the charge consists of a predetermined amount of casting material which substantially fills the female mold.

9. The method of claim 1, wherein:

the female mold is rotated about a vertical axis.

10. The method of claim 1, wherein:

the female mold is rotated about a horizontal axis.

11. The method of claim 1, wherein:

the female mold is rotated bi-axially.

12. The method of claim 1, wherein:

the network of grooves are configured with undulations.

13. The method of claim 1, wherein:

the cavity is rotating about the rotational axis when the charge is introduced.

14. The method of claim 1, wherein:

the female mold starts to rotate about the axis after the charge of casting material is introduced.

15. The method of claim 1, wherein:

selecting a female mold includes selecting a mold formed with an elongated cavity having an annular wall formed with a network of grooves cooperating to form the outline of an expanded stent.

16. The method of claim 1, wherein:

the stent is formed in a radially compressed condition.

17. The method of claim 1, wherein:

the rotating step includes rotating the female mold cavity at a sufficient tangential velocity to provide a centrifugal acceleration of greater than 1G.

18. The method of claim 1, wherein:

the female mold is formed with a plurality of circumferential grooves having a continuous undulating pattern formed by a plurality of U-shaped pathways linked together in a consecutive alternating inverted relationship; and at least one interconnecting channel extends longitudinally between adjacent circumferential grooves connecting them together.

19. The method of claim 1, wherein:

the casting material is biocompatible.

20. The method of claim 1, wherein:

the casting material is liquid or pourable metal.

21. The method of claim 1, wherein:

the casting material is liquid or pourable plastic.

22. The method of claim 1, wherein:

the casting material is a powdered polymer.

23. The method of claim 1, wherein:

the casting material is a powdered polymer combined with a drug agent.

24. The method of claim 1, wherein:

the casting material is made from a bioabsorbable material.

25. A method of making a stent of a predetermined configuration including:

selecting a female mold formed with an elongated cavity having an angular wall formed with a network of grooves cooperating to form a predetermined stent configuration;

introducing a charge of casting material into the cavity;

rotating the female mold about a rotational axis to distribute the casting material throughout the network of grooves to form the predetermined configuration;

heating the female mold as it is being rotated about the rotational axis for a predetermined time interval;

cooling the female mold after the expiration of the time period for heating the female mold to allow the female mold and casting material to cool; and solidifying the casting material to form the stent.

26. The method of claim 25, wherein:

the casting material is a powdered polymer.

27. The method of claim 25, wherein:

the casting material is a powdered polymer combined with a drug agent.

* * * * *